United States Patent
Matsuda et al.

(10) Patent No.: US 10,258,611 B2
(45) Date of Patent: Apr. 16, 2019

(54) COMBINATION OF IBUDILAST AND RILUZOLE AND METHODS OF USING SAME

(71) Applicant: MEDICINOVA, INC., La Jolla, CA (US)

(72) Inventors: Kazuko Matsuda, La Jolla, CA (US); Yuichi Iwaki, La Jolla, CA (US)

(73) Assignee: MediciNova, Inc., La Jolla, CA (US)

( * ) Notice: Subject to any disclaimer, the term of this patent is extended or adjusted under 35 U.S.C. 154(b) by 0 days.

(21) Appl. No.: 15/527,280

(22) PCT Filed: Nov. 24, 2015

(86) PCT No.: PCT/US2015/062456
§ 371 (c)(1),
(2) Date: May 16, 2017

(87) PCT Pub. No.: WO2016/085998
PCT Pub. Date: Jun. 2, 2016

(65) Prior Publication Data
US 2017/0360762 A1    Dec. 21, 2017

Related U.S. Application Data

(60) Provisional application No. 62/084,879, filed on Nov. 26, 2014.

(51) Int. Cl.
| | | |
|---|---|---|
| *A61K 31/437* | (2006.01) |
| *A61K 31/428* | (2006.01) |
| *A61K 9/00* | (2006.01) |
| *A61K 9/08* | (2006.01) |
| *A61K 9/20* | (2006.01) |
| *A61K 9/48* | (2006.01) |

(52) U.S. Cl.
CPC .......... *A61K 31/437* (2013.01); *A61K 9/0053* (2013.01); *A61K 9/08* (2013.01); *A61K 9/20* (2013.01); *A61K 9/48* (2013.01); *A61K 31/428* (2013.01)

(58) Field of Classification Search
None
See application file for complete search history.

(56) References Cited

U.S. PATENT DOCUMENTS

| | | | |
|---|---|---|---|
| 4,788,055 A | 11/1988 | Fischer et al. |
| 4,816,264 A | 3/1989 | Phillips et al. |
| 4,828,836 A | 5/1989 | Elger et al. |
| 4,834,965 A | 5/1989 | Martani et al. |
| 4,834,985 A | 5/1989 | Elger et al. |
| 4,996,047 A | 2/1991 | Kelleher et al. |
| 5,071,646 A | 12/1991 | Malkowska et al. |
| 5,133,974 A | 7/1992 | Paradissis et al. |
| 9,114,136 B2 * | 8/2015 | Kalafer ............... A61K 31/437 |
| 2006/0160843 A1 | 7/2006 | Johnson et al. |
| 2009/0062330 A1 | 3/2009 | Kalafer et al. |
| 2014/0171463 A1 | 6/2014 | Kalafer et al. |

FOREIGN PATENT DOCUMENTS

| | | |
|---|---|---|
| WO | WO 2004/105756 A2 | 12/2004 |
| WO | WO 2005/084377 A2 | 9/2005 |

OTHER PUBLICATIONS

Zhang, W. et al., Bioorg. Med. Chem. vol. 20, pp. 1029-1045, 2012.*
International Preliminary Report on Patentability issued in related International Patent Application No. PCT/US2015/062456, dated Jun. 8, 2017.
International Search Report and Written Opinion issued in related International Patent Application No. PCT/US2015/062456, dated Feb. 9, 2016.
MEDLIBRARY.ORG. Rilutek. Nov. 2012. [Retrieved on Jan. 5, 2016 from the internet, http://medlibrary.org/lib/rx/meds/rilutek, 2 pages].
Lee et al., "Ibudilast, a Phosphodiesterase Inhibitor with Anti-Inflammatory Activity, Protects Against Ischemic Brain Injury in Rats," *Brain Research 1431*, pp. 97-106 (2012).
NCT02238626 Clinical Trials.GOV., Ibudilast (MN-166) in Subjects with Amyotrophic Lateral Sclerosis (ALS), Sep. 11, 2014, 5 pages.
NCT01982942 Clinical Trials.GOV., Safety, Tolerability and Activity Study of Ibudilast in Subjects with Progressive Multiple Sclerosis, Nov. 12, 2013, 6 pages.
Vesterinen, et al., "Drug Repurposing: A Systematic Approach to Evaluate Candidate Oral Neuroprotective Interventions for Secondary Progressive Multiple Sclerosis," *PLUS One*, vol. 10, No. 4, pp. 1-18 (Apr. 2015).
Sibon et al., "American Academy of Neurology, Washington, Apr. 18-25, 2015," *Revue Nerologi*, vol. 171, No. 6-7, pp. 581-601 (Jun. 2015), Eng. Abstract provided.
Search Report issue in European Patent Application No. 15 86 3670, dated May 28, 2018.

* cited by examiner

*Primary Examiner* — Heidi Reese
(74) *Attorney, Agent, or Firm* — Foley & Lardner LLP

(57) ABSTRACT

The present disclosure relates generally to methods for treating neurodegenerative diseases, including their progressive forms. In particular, the present disclosure pertains to methods of treating or preventing neurodegenerative diseases, including their progressive forms and their associated symptoms by administering a combination of ibudilast (3-isobutyryl-2-isopropylpyrazolo[1,5-a]pyridine) and riluzole, or pharmaceutically acceptable salts of one or both thereof.

10 Claims, 1 Drawing Sheet

COMBINATION OF IBUDILAST AND RILUZOLE AND METHODS OF USING SAME

CROSS-REFERENCE TO RELATED APPLICATION

This application is a National Stage Entry of International Patent Application No. PCT/US2015/062456, filed May 10, 2016, which claims the benefit of the priority date of U.S. Provisional Application No. 62/084,879, filed Nov. 26, 2014, the contents of which are incorporated herein by reference in their entirety.

FIELD OF THE DISCLOSURE

The present disclosure relates generally to methods for treating neurodegenerative diseases, including those which are of the progressive variety. For example, the present invention pertains to methods of treating or preventing progressive neurodegenerative diseases and its associated symptoms by administration of a combination of ibudilast (3-isobutyryl-2-isopropylpyrazolo [1,5-a]pyridine) and riluzole (2-amino-6-(trifluoromethoxy) benzothiazole).

BACKGROUND OF THE DISCLOSURE

Ibudilast

Ibudilast is a small molecule drug (molecular weight of 230.3) having the structure shown below.

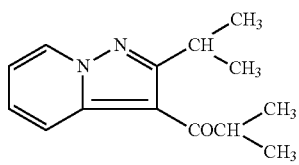

(I)

Ibudilast is also found under ChemBank ID 3227, CAS # 50847-11-5, and Beilstein Handbook Reference No. 5-24-03-00396. Its molecular formula corresponds to $C_{14}H_{18}N_2O$. Ibudilast is also known by various chemical names including 2-methyl-1-(2-(1-methylethyl)pyrazolo(1, 5-a)pyridin-3-yl)1-propanone; 3-isobutyryl-2-isopropylpyrazolo (1,5-a)pyridine]; and 1-(2-isopropyl-pyrazolo [1,5-a]pyridin-3-yl)-2-methyl-propan-1-one. Other synonyms for ibudilast include Ibudilastum (Latin), BRN 0656579, KC-404, and MN-166. Its brand name is Ketas-$^{RTM}$. Ibudilast, as referred to herein, is meant to include any and all pharmaceutically acceptable salt forms thereof, pro-drug forms (e.g., the corresponding ketal), solvates, and the like, as appropriate for use in its intended formulation for administration.

Ibudilast has been widely used in Japan for relieving symptoms associated with ischemic stroke or bronchial asthma. Marketed indications for ibudilast in Japan include its use as a vasodilator, for treating allergy, eye tissue regeneration, ocular disease, and treatment of allergic ophthalmic disease (Thompson Current Drug Reports). US Patent Application Publication No. 2009/0062330 discloses the treatment of progressive neurodegenerative diseases by the administration of ibudilast. This publication generally discloses that ibudilast may be administered in a combination treatment along with an additional agent effective for treating progressive neurodegenerative diseases, but does not provide any guidance on the choice of the additional agent.

Riluzole

Riluzole has the formula:

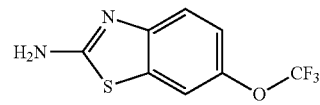 [SMILES: Nc1nc2ccc(OC(F)(F)F)cc2s1]

and is indicated for the treatment of patients with amyotrophic lateral sclerosis (ALS). Chemically, riluzole is 2-amino-6-(trifluoromethoxy) benzothiazole.

SUMMARY OF THE DISCLOSURE

The present disclosure relates to a novel approach to treating a neurodegenerative disease or disorder, including progressive forms, and is based on the administration of a combination of ibudilast and riluzole.

Accordingly, in one embodiment, the present disclosure is a method of alleviating negative effects of a neurodegenerative disease or disorder in a human patient suffering therefrom, comprising administering to the human patient in need thereof:
  (a) a therapeutically effective amount of ibudilast or a pharmaceutically acceptable salt thereof, and
  (b) a therapeutically effective amount of riluzole or a pharmaceutically acceptable salt thereof.

In one embodiment, the disclosure is a method of slowing progression of disease in a patient diagnosed with a chronic neurodegenerative disease, comprising administering to the patient:
  (a) a therapeutically effective amount of ibudilast or a pharmaceutically acceptable salt thereof, and
  (b) a therapeutically effective amount of riluzole or a pharmaceutically acceptable salt thereof.

In another embodiment, the disclosure is a method of treating a patient diagnosed with a neurodegenerative disease or disorder, comprising administering to the patient:
  (a) a therapeutically effective amount of ibudilast or a pharmaceutically acceptable salt thereof, and
  (b) a therapeutically effective amount of riluzole or a pharmaceutically acceptable salt thereof.

In one embodiment, the neurodegenerative disease or disorder is Alzheimer's disease, Senile dementia of the Alzheimer type, Pick's disease (lobar atrophy), syndromes combining progressive dementia with other prominent neurologic abnormalities, Huntington's disease, multiple system atrophy combining dementia with ataxia and/or manifestation of Parkinson's disease, progressive supranuclear palsy (Steele-Richardson-Olszewski), diffuse Lewy body disease, corticodentatinigral degeneration, Hallervorden-Spatz disease, progressive familial myoclonic epilepsy, symptoms of gradually developing abnormalities of posture and movement, paralysis agitans (Parkinson's disease), striatonigral degeneration, progressive supranuclear palsy, torsion dystonia (torsion spasm; dystonia musculorum deformans), spasmodic torticollis and other restricted dyskinesias, Familial tremor, Gilles de la Tourette syndrome, progressive ataxia, cerebellar degenerations, spinocerebellar degenerations, cerebellar cortical degeneration, olivopontocerebellar atrophy (OPCA), spinocerebellar degenerations (Friedreich's ataxia and related disorders), central autonomic nervous system failure (Shy-Drager syndrome), syndromes of muscular weakness and wasting without sensory changes (motor neuron disease), amyotrophic lateral sclerosis (ALS), spinal muscular atrophy, infantile spinal muscular atrophy (Werdnig-Hoffmann), juvenile spinal muscular atrophy (Wohlfart-Kugelberg-Welander), other forms of familial spinal muscular atrophy, primary lateral sclerosis, hereditary spastic paraplegia, syndromes combining muscular weakness and wasting with sensory changes (progressive neural muscular atrophy; chronic familial polyneuropathies), peroneal muscular atrophy (Charcot-Marie-Tooth), hypertrophic interstitial polyneuropathy (Deferine-Sottas), or miscellaneous forms of chronic progressive neuropathy, syndromes of progressive visual loss, pigmentary degeneration of the retina (retinitis pigmentosa), hereditary optic atrophy (Leber's disease), Parkinson's disease and other extrapyramidal disorders, progressive supranuclear palsy (Steele-Richardson-Olszewski syndrome), torsion dystonia (torsion spasm, dystonia musculorum deformans), focal dystonias, motor neuron disease, progressive ataxias, primary lateral sclerosis, multifocal motor neuropathy with conduction block, motor neuropathy with paraproeinemia, motor-predominant peripheral neuropathies, olivopontocerebellar atrophy, Azorean (Machado-Joseph) disease, familial progressive neurodegenerative diseases, familial amyotrophic lateral sclerosis, spinal muscular atrophies, familial spastic paraparesis, hereditary biochemical disorders, arthrogryposis muliplex congenital, or progressive juvenile bulbar palsy (Fazio-Londe), infantile (Werdnig-Hoffman disease), childhood onset, or adolescent (Wohlfart-Kugelberg-Welander disease), familial HTLV-1 myelopathy, isolated FSP, or complicated FSP, superoxide dismutase deficiency, hexosaminidase A and B deficiency, androgen receptor mutation (Kennedy's syndrome), viral and prion diseases, myelopathy, progressive multifocal leukoencephalopathy, Creutzfeldt-Jakob disease, Gerstmann-Straussler-Scheinker disease, kuru, fatal familial insomnia, Alper's disease, primary progressive or secondary progressive multiple sclerosis, but not relapsing, remitting multiple sclerosis, frontotemporal dementia, Wilson's disease, progressive neuropathic pain, ischemia caused by stroke, traumatic brain injury, or spinal cord injury.

In one embodiment, the neurodegenerative disease is of the progressive type.

In another embodiment, the neurodegenerative disease or disorder is Alzheimer's disease, Parkinson's disease, amyotrophic lateral sclerosis (ALS), or multiple sclerosis. In a specific embodiment, the neurodegenerative disease or disorder is ALS.

In one embodiment, the disclosure is a method of reducing a volume of an infarct (an area of necrosis in a tissue or organ resulting from obstruction of the local circulation by a thrombus or embolus) in a patient suffering from an ischemia, comprising administering to a patient in need thereof:
 (a) a therapeutically effective amount of ibudilast or a pharmaceutically acceptable salt thereof, and
 (b) a therapeutically effective amount of riluzole or a pharmaceutically acceptable salt thereof,
in which a volume of an infarct in the treated patient is reduced compared to a volume of an infarct in a control patient.

In one embodiment, the ibudilast and riluzole, or pharmaceutically acceptable salts thereof are administered orally.

In one embodiment, ibudilast and riluzole, or pharmaceutically acceptable salts thereof, are administered in separate dosage forms. In another embodiment, ibudilast and the riluzole, or pharmaceutically acceptable salts thereof, are administered in the same dosage form. Also the ibudilast and riluzole, if present in separate dosage forms, may be administered concurrently or at different times.

In one embodiment, the ibudilast or a pharmaceutically acceptable salt thereof is administered in an amount from about 100 to about 4,000 mg/day, divided into one, two, or three portions. In another embodiment, the riluzole or pharmaceutically acceptable salt thereof is administered in an amount from about 1 mg/kg to about 1000 mg/kg of the patient, divided into one, two, or three portions. In a particular embodiment, the riluzole or pharmaceutically acceptable salt thereof is administered at a total dose of from about 10 mg per day to about 500 mg per day. In another embodiment, the riluzole or pharmaceutically acceptable salt thereof is administered once a day at a dose of from about 10 mg to about 500 mg. In another embodiment, the riluzole or pharmaceutically acceptable salt thereof is administered twice a day at a total dose of from about 10 mg per day to about 500 mg per day.

In one embodiment, the disclosure is a composition, comprising:
 (a) ibudilast or a pharmaceutically acceptable salt thereof,
 (b) riluzole or a pharmaceutically acceptable salt thereof, and
 (c) optionally, a pharmaceutically acceptable excipient or carrier.

In one embodiment, the composition comprises from about 100 to about 4,000 mg of ibudilast or a pharmaceutically acceptable salt thereof and from about 10 to about 500 mg of riluzole or a pharmaceutically acceptable salt thereof.

In one embodiment, the composition is an oral tablet or capsule. In another embodiment, the composition is an oral liquid dosage form.

DETAILED DESCRIPTION

Figure 1:
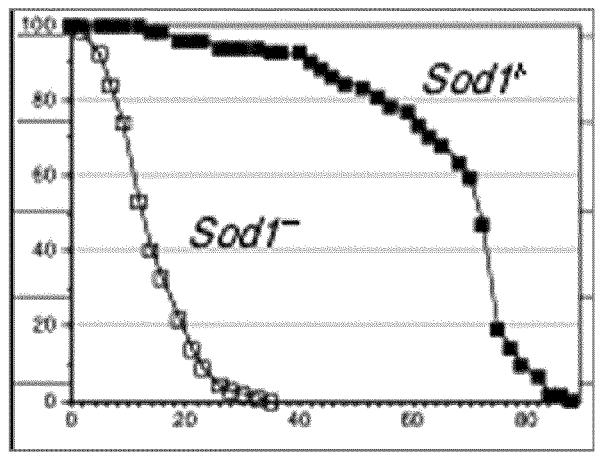
FIG. 1 graphically illustrates comparative life span in Sod1 mutants (Sod1l$^-$) and wt (Sod1+). Maximum life span of mutants is 25-30 days compared to 70-80 days for controls; recovering on life span curve can indicate positive compound activity.

The practice of the present disclosure will employ, unless otherwise indicated, conventional methods of chemistry, biochemistry, and pharmacology, within the skill of the art. Such techniques are explained fully in the literature. See, e.g.; A. L. Lehninger, Biochemistry (Worth Publishers, Inc., current addition); Morrison and Boyd, Organic Chemistry (Allyn and Bacon, Inc., current addition); J. March, Advanced Organic Chemistry (McGraw Hill, current addition); Remington: The Science and Practice of Pharmacy, A. Gennaro, Ed., 20th Ed.; FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

All publications cited herein, including internet articles, the FDA Orange Book (available on the FDA's website), books, handbooks, journal articles, patents and patent applications, whether supra or infra, are hereby incorporated by reference in their entirety.

Definitions

It must be noted that, as used in this specification and the intended claims, the singular forms "a," "an," and "the" include plural referents unless the context clearly dictates otherwise. Thus, for example, reference to "a drug" includes a single drug as well as two or more of the same or different drugs, reference to "an optional excipient" refers to a single optional excipient as well as two or more of the same or different optional excipients, and the like.

"Administering" or "administration of" a drug to a patient (and grammatical equivalents of this phrase) includes both direct administration, including self-administration, and indirect administration, including the act of prescribing a drug. For example, as used herein, a physician who instructs a patient to self-administer a drug and/or provides a patient with a prescription for a drug is administering the drug to the patient.

"Comprising" shall mean that the methods and compositions include the recited elements, but not exclude others. "Consisting essentially of" when used to define methods and compositions, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this disclosure or process steps to produce a composition or achieve an intended result. Embodiments defined by each of these transitional terms and phrases are within the scope of this disclosure.

"Effective amount" of a compound utilized herein is an amount that, when administered to a patient treated as herein, will have the intended therapeutic effect, e.g., alleviation, amelioration, palliation or elimination of one or more manifestations of the medical condition in the patient. The full therapeutic effect does not necessarily occur by administration of one dose (or dosage), and may occur only after administration of a series of doses. Thus, an effective amount may be administered in one or more administrations.

"Pharmaceutically acceptable" refers to non-toxic and suitable for administration to a patient, including a human patient.

"Pharmaceutically acceptable salts" refer to salts that are non-toxic and are suitable for administration to patients. "Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

"Treating" a medical condition or a patient refers to taking steps to obtain beneficial or desired results, including clinical results. For purposes of the various aspects and embodiments of the present disclosure, beneficial or desired clinical results include, but are not limited to, reduction, alleviation, or amelioration of one or more manifestations of or negative effects of ALS, PLS or familial ALS, improvement in one or more clinical outcomes, diminishment of extent of sclerosis, delay or slowing of sclerosis progression, amelioration, palliation, or stabilization of the scleroses state, and other beneficial results described herein.

By "neurodegenerative disease" means any neurodegenerative disease that causes the loss of structure or function of neurons in the nervous system of an individual, including death of neurons. Neurodegenerative disease includes progressive neurodegenerative diseases, in which the symptoms worsen over time. In certain instances, the symptoms worsen at a gradual rate. Examples of progressive neurodegenerative diseases include Alzheimer's Disease, Parkinsonism and amyotrophic lateral sclerosis. An example of a neurodegenerative disease is a relapsing and remitting form of multiple sclerosis (MS). MS also exhibits progressive forms.

The term "central nervous system" or "CNS" includes all cells and tissue of the brain and spinal cord of a vertebrate. Thus, the term includes, but is not limited to, neuronal cells, glial cells, astrocytes, cerebrospinal fluid (CSF), interstitial spaces and the like.

The terms "subject," "individual," or "patient" are used interchangeably herein and refer to a vertebrate, preferably a mammal. Mammals include, but are not limited to, murines, rodents, simians, humans, farm animals, sport animals and pets.

The terms "pharmacologically effective amount" or "therapeutically effective amount" of a composition or agent, as provided herein, refer to a nontoxic but sufficient amount of the composition or agent to provide the desired response, such as a reduction, alleviation, or reversal of the symptoms of neurodegenerative diseases. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The term "about," particularly in reference to a given quantity, is meant to encompass deviations of plus or minus five percent.

As stated previously, a reference to any one or more of the herein-described drugs, in particular ibudilast, is meant to encompass, where applicable, any and all enantiomers, mixtures of enantiomers including racemic mixtures, prodrugs, pharmaceutically acceptable salt forms, hydrates (e.g., monohydrates, dihydrates, etc.), solvates, different physical forms (e.g., crystalline solids, amorphous solids), metabolites, and the like.

Methods of Treatment

In one embodiment, the disclosure is a method of alleviating negative effects of a neurodegenerative disease or disorder in a human patient suffering therefrom, comprising administering to a patient in need thereof:
   (a) a therapeutically effective amount of ibudilast or a pharmaceutically acceptable salt thereof, and
   (b) a therapeutically effective amount of riluzole or a pharmaceutically acceptable salt thereof.

In one embodiment, the disclosure is a method of slowing progression of disease in a patient diagnosed with a chronic neurodegenerative disease, comprising administering to the patient:
(a) a therapeutically effective amount of ibudilast or a pharmaceutically acceptable salt thereof, and
(b) a therapeutically effective amount of riluzole or a pharmaceutically acceptable salt thereof.

In another embodiment, the disclosure is a method of treating a patient diagnosed with a neurodegenerative disease or disorder, comprising administering to the patient:
(a) a therapeutically effective amount of ibudilast or a pharmaceutically acceptable salt thereof, and
(b) a therapeutically effective amount of riluzole or a pharmaceutically acceptable salt thereof.

In one embodiment, the neurodegenerative disease or disorder compromises the nervous system.

In another embodiment, the neurodegenerative disease or disorder is Alzheimer's disease, Senile dementia of the Alzheimer type, Pick's disease (lobar atrophy), syndromes combining progressive dementia with other prominent neurologic abnormalities, Huntington's disease, multiple system atrophy combining dementia with ataxia and/or manifestation of Parkinson's disease, progressive supranuclear palsy (Steele-Richardson-Olszewski), diffuse Lewy body disease, corticodentatinigral degeneration, Hallervorden-Spatz disease, progressive familial myoclonic epilepsy, symptoms of gradually developing abnormalities of posture and movement, paralysis agitans (Parkinson's disease), striatonigral degeneration, progressive supranuclear palsy, torsion dystonia (torsion spasm; dystonia musculorum deformans), spasmodic torticollis and other restricted dyskinesias, Familial tremor, Gilles de la Tourette syndrome, progressive ataxia, cerebellar degenerations, spinocerebellar degenerations, cerebellar cortical degeneration, olivopontocerebellar atrophy (OPCA), spinocerebellar degenerations (Friedreich's ataxia and related disorders), central autonomic nervous system failure (Shy-Drager syndrome), syndromes of muscular weakness and wasting without sensory changes (motor neuron disease), amyotrophic lateral sclerosis (ALS), spinal muscular atrophy, infantile spinal muscular atrophy (Werdnig-Hoffmann), juvenile spinal muscular atrophy (Wohlfart-Kugelberg-Welander), other forms of familial spinal muscular atrophy, primary lateral sclerosis, hereditary spastic paraplegia, syndromes combining muscular weakness and wasting with sensory changes (progressive neural muscular atrophy; chronic familial polyneuropathies), peroneal muscular atrophy (Charcot-Marie-Tooth), hypertrophic interstitial polyneuropathy (Deferine-Sottas), or miscellaneous forms of chronic progressive neuropathy, syndromes of progressive visual loss, pigmentary degeneration of the retina (retinitis pigmentosa), hereditary optic atrophy (Leber's disease), Parkinson's disease and other extrapyramidal disorders, progressive supranuclear palsy (Steele-Richardson-Olszewski syndrome), torsion dystonia (torsion spasm, dystonia musculorum deformans), focal dystonias, motor neuron disease, progressive ataxias, primary lateral sclerosis, multifocal motor neuropathy with conduction block, motor neuropathy with paraproeinemia, motor-predominant peripheral neuropathies, olivopontocerebellar atrophy, Azorean (Machado-Joseph) disease, familial progressive neurodegenerative diseases, familial amyotrophic lateral sclerosis, spinal muscular atrophies, familial spastic paraparesis, hereditary biochemical disorders, arthrogryposis muliplex congenital, or progressive juvenile bulbar palsy (Fazio-Londe), infantile (Werdnig-Hoffman disease), childhood onset, or adolescent (Wohlfart-Kugelberg-Welander disease), familial HTLV-1 myelopathy, isolated FSP, or complicated FSP, superoxide dismutase deficiency, hexosaminidase A and B deficiency, androgen receptor mutation (Kennedy's syndrome), viral and prion diseases, myelopathy, progressive multifocal leukoencephalopathy, Creutzfeldt-Jakob disease, Gerstmann-Straussler-Scheinker disease, kuru, fatal familial insomnia, Alper's disease, primary progressive or secondary progressive multiple sclerosis, but not relapsing, remitting multiple sclerosis, frontotemporal dementia, Wilson's disease, progressive neuropathic pain, ischemia caused by stroke, traumatic brain injury, or spinal cord injury.

In one embodiment, the neurodegenerative disease is of the progressive type.

In a particular embodiment, the neurodegenerative disease or disorder is Alzheimer's disease, Parkinson's disease, amyotrophic lateral sclerosis (ALS), or multiple sclerosis. In a particular embodiment, the neurodegenerative disease or disorder is ALS.

In one embodiment, the disclosure is a method of reducing a volume of an infarct (an area of necrosis in a tissue or organ resulting from obstruction of the local circulation by a thrombus or embolus) in a patient suffering from an ischemia, comprising administering to a patient in need thereof:
(a) a therapeutically effective amount of ibudilast or a pharmaceutically acceptable salt thereof, and
(b) a therapeutically effective amount of riluzole or a pharmaceutically acceptable salt thereof,
in which a volume of an infarct in the treated patient is reduced compared to a volume of an infarct in a control patient.

Methods of Administration

In some embodiments, the present disclosure comprises administering ibudilast and riluzole, or pharmaceutically acceptable salts thereof, either systemically or centrally (e.g., by intrathecal administration, i.e., into the cerebrospinal fluid surrounding the spinal cord). In a further embodiment, the present disclosure comprises administering ibudilast and riluzole, or pharmaceutically acceptable salts thereof, systemically, e.g., via parenteral, enteral, oral, intravenous, intranasal, sublingual or other systemic routes, to a human, subject for the treatment of progressive neurodegenerative diseases.

In a particular embodiment, the present disclosure comprises administering ibudilast and riluzole, or pharmaceutically acceptable salts thereof, orally.

In one embodiment, the disclosure comprises administering ibudilast and riluzole, or pharmaceutically acceptable salts thereof as a single combination composition. In terms of patient compliance and ease of administration, such an approach is preferred, since patients are often adverse to taking multiple pills or dosage forms, often multiple times daily, over the duration of treatment. Alternatively, in another embodiment, ibudilast and riluzole, or pharmaceutically acceptable salts thereof are administered as separate dosage forms. In embodiments in which ibudilast and riluzole, or pharmaceutically acceptable salts thereof are administered as separate dosage forms, ibudilast and riluzole, or pharmaceutically acceptable salts thereof may be administered simultaneously, sequentially in any order, or separately.

Doses and Dosage Forms

In one embodiment, the disclosure is a composition, comprising:
(a) ibudilast or a pharmaceutically acceptable salt thereof, (b) riluzole or a pharmaceutically acceptable salt thereof, and (c) optionally, a pharmaceutically acceptable excipient or carrier.

In one embodiment, the disclosure is a composition, comprising:

(a) from about 100 to about 4,000 mg/day of ibudilast or a pharmaceutically acceptable salt thereof, (b) from about 50 mg to about 4,000 mg of riluzole or a pharmaceutically acceptable salt thereof, and (c) optionally, a pharmaceutically acceptable excipient or carrier.

In other embodiments, the disclosure is a composition, comprising:

(a) a therapeutically effective amount of ibudilast or a pharmaceutically acceptable salt thereof, (b) a therapeutically effective amount of riluzole or a pharmaceutically acceptable salt thereof, and (c) optionally, a pharmaceutically acceptable excipient or carrier, wherein the composition is effective to alleviate the negative effects of a neurodegenerative disease or disorder in a human patient suffering therefrom.

Therapeutically effective amounts can be determined by those skilled in the art, and will be adjusted to the requirements of each particular case. Effective dosage levels of ibudilast can vary from about 100 to about 4000 mg per day. In one embodiment, the daily dosage range is 250 to 2,000 mg, given in one, two, or three portions. In one embodiment, the daily dosage range of ibudilast is 100 to 500 mg, such as 100, 200, 300, 400, or 500 mg given in one, two, or three portions. In one embodiment, the daily dosage range of ibudilast is about 250 to about 2,000 mg, such as 250, 500, 750, 1,000, 1,250, 1,500, 1,750, or 2,000 mg given in one, two, or three portions. In one embodiment, the daily dosage range of ibudilast is from about 1000 to about 4,000 mg, such as about 1,000, about 2,000, about 3,000, or about 4,000 mg, given in one, two, or three portions. In another embodiment, the dosage is about 1000 mg twice a day. In other embodiments, suitable dosages of ibudilast include about 1000 mg four times a day, about 1000 mg twice a day, and about 750 mg three times a day.

An effective dose of riluzole in a composition of the present disclosure is from about 0.1 mg/kg/day to about 4,000 mg/kg/day, or from about 1 mg/kg/day to about 50 mg/kg/day, or from about 1 mg/kg/day to about 25 mg per kg/day. In other embodiments, the effective amount of riluzole is from about 1 mg/kg/day to about 1000 mg/kg/day given in one, two, or three portions. In some other embodiments, the effective amount of riluzole is from about 10 mg/kg/day to about 100 mg/kg/day, about 20 mg/kg/day to about 90 mg/kg/day, about 30 mg/kg/day to about 80 mg/kg/day, about 40 mg/kg/day to about 70 mg/kg/day, or about 50 mg/kg/day to about 60 mg/kg/day. In still some other embodiments, the dose of riluzole is from about 100 mg/kg/day to about 1000 mg/kg/day. In particular embodiments, the total dose of riluzole about 10 mg/day to about 500 mg/day. In some embodiments, the daily dose of riluzole is given in one, two, or three portions.

Actual amounts will depend on the circumstances of the patient being treated. As those skilled in the art recognize, many factors that modify the action of the active substance will be taken into account by the treating physician such as the age, body weight, sex, diet and condition of the patient, the time of administration, the rate and route of administration. Optimal dosages for a given set of conditions can be ascertained by those skilled in the art using conventional dosage determination tests.

The compounds utilized herein can be formulated in any pharmaceutically acceptable form, including liquids, powders, creams, emulsions, pills, troches, suppositories, suspensions, solutions, and the like. Compositions according to the present disclosure will ordinarily be formulated with one or more pharmaceutically acceptable ingredients in accordance with known and established practice. In general, tablets are formed utilizing a carrier such as modified starch, alone or in combination with carboxymethyl cellulose (Avicel), for example at about 10% by weight. The formulations are compressed at from 1,000 to 3,000 pounds pressure in the tablet forming process. The tablets preferably exhibit an average hardness of about 1.5 to 8.0 kp/cm$^2$, preferably 5.0 to 7.5 kp/cm$^2$. Disintegration time varies from about 30 seconds to about 15 or 20 minutes.

Compositions for oral use can be provided as hard gelatin capsules wherein the therapeutically active compounds utilized herein are mixed with an inert solid diluent such as calcium carbonate, calcium phosphate or kaolin, or as soft gelatin capsules in which the compounds are mixed with an oleaginous medium, e.g., liquid paraffin or olive oil. Suitable carriers include magnesium carbonate, magnesium stearate, talc, sugar, lactose, pectin, dextrin, starch, gelatin, tragacanth, methylcellulose, sodium carboxymethyl cellulose, a low melting wax, cocoa butter, and the like.

The compositions of the present disclosure can be formulated as aqueous suspensions in admixture with pharmaceutically acceptable excipients such as suspending agents including, but not limited to, sodium carboxymethyl cellulose, methylcellulose, hydroxypropylmethyl cellulose, sodium alginate, polyvinylpyrrolidone, gum tragacanth and gum acacia; dispersing or wetting agents such as naturally occurring phosphatide, e.g., lecithin, or condensation products of an alkaline oxide with fatty acids, e.g., polyoxyethylene stearate, or condensation products of ethylene oxide with long chain aliphatic alcohols, e.g., heptadecaethyleneoxycetanol, or condensation products of ethylene oxide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monoleate. Such aqueous suspensions can also contain one or more preservatives, e.g., ethyl- or n-propyl-p-hydroxy benzoate, one or more coloring agents, one or more flavoring agents and one or more sweetening agents, such as glycerol, sorbitol, sucrose, saccharin or sodium or calcium cyclamate.

Suitable compositions of the present disclosure also include sustained release dosage forms, such as those described in U.S. Pat. Nos. 4,788,055; 4,816,264; 4,828,836; 4,834,965; 4,834,985; 4,996,047; 5,071,646; and, 5,133,974, the contents of which are incorporated herein in their entirety by reference.

Other compositions of the present disclosure suitable for oral administration include liquid form preparations including emulsions, syrups, elixirs, aqueous solutions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Solid form preparations may contain, in addition to the active component, colorants, flavors, stabilizers, buffers, artificial and natural sweeteners, dispersants, thickeners, solubilizing agents, and the like.

The compositions of the present disclosure may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example as solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compositions of the present disclosure can be formulated for nasal administration. The solutions or suspensions are applied directly to the nasal cavity by conventional means, for example, with a dropper, pipette or spray. The formulations may be provided in a single or multidose form. The patient can administer an appropriate, predetermined volume of the solution or suspension via a dropper or pipette. A spray may be administered for example by means of a metering atomizing spray pump.

The compositions of the present disclosure can be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC), (for example, dichlorodifluoromethane, trichlorofluoromethane, or dichlorotetrafluoroethane), carbon dioxide or other suitable gases. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine. The powder carrier will form a gel in the nasal cavity. The powder composition may be presented in unit dose form for example in capsules or cartridges of, for example gelatin or blister packs from which the powder may be administered by means of an inhaler.

The compositions of the present disclosure may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges including active agents in a flavored base, usually sucrose and acacia or tragacanth; pastilles including the active ingredient in an inert base such as gelatin and glycerin or sucrose and acacia; and mouthwashes including the active ingredient in a suitable liquid carrier.

The compositions of the present disclosure may be formulated for administration as suppositories. In such a formulation, a low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compositions of the present disclosure may be formulated for vaginal administration. Pessaries, tampons, creams, gels, pastes, foams or sprays containing in addition to the active ingredient such carriers as are known in the art to be appropriate.

Oral Compositions

Oral compositions of the present disclosure may further comprise one or more pharmaceutically acceptable excipients or carriers. Exemplary excipients include, without limitation, polyethylene glycol (PEG), hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

A composition of the disclosure may include one or more carbohydrates such as a sugar, a derivatized sugar such as an alditol, aldonic acid, an esterified sugar, and/or a sugar polymer. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Also suitable for use in the compositions of the disclosure are potato and corn-based starches such as sodium starch glycolate and directly compressible modified starch.

Further representative excipients include inorganic salt or buffers such as citric acid, sodium chloride, potassium chloride, sodium sulfate, potassium nitrate, sodium phosphate monobasic, sodium phosphate dibasic, and combinations thereof.

A composition of the disclosure may also include an antimicrobial agent, e.g., for preventing or deterring microbial growth. Non-limiting examples of antimicrobial agents suitable for the present disclosure include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

A composition of the disclosure may also contain one or more antioxidants. Antioxidants are used to prevent oxidation, thereby preventing the deterioration of the drug(s) or other components of the preparation. Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition of the disclosure may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the role of the excipient, the dosage requirements of the active agent components, and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient. In general, the amount of excipient present in a composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

Modified Release Compositions

When desired, compositions of the present disclosure can be prepared with enteric coatings adapted for sustained or controlled release administration of the active ingredient. A common type of controlled release formulation that may be used for the purposes of the present disclosure comprises an inert core, such as a sugar sphere, a first layer, coated with an inner drug-containing second layer, and an outer membrane or third layer controlling drug release from the inner layer.

The cores are preferably of a water-soluble or swellable material, and may be any such material that is conventionally used as cores or any other pharmaceutically acceptable water-soluble or water-swellable material made into beads or pellets. The cores may be spheres of materials such as sucrose/starch (Sugar Spheres NF), sucrose crystals, or extruded and dried spheres typically comprised of excipients such as microcrystalline cellulose and lactose.

The substantially water-insoluble material in the first layer is generally a "GI insoluble" or "GI partially insoluble" film forming polymer (dispersed or dissolved in a solvent). As examples may be mentioned ethyl cellulose, cellulose acetate, cellulose acetate butyrate, polymethacrylates such as ethyl acrylate/methyl methacrylate copolymer (Eudragit NE-30-D) and ammonio methacrylate copolymer types A and B (Eudragit RL30D and RS30D), and silicone elastomers. Usually, a plasticizer is used together with the polymer. Exemplary plasticizers include: dibutylsebacate, propylene glycol, triethylcitrate, tributylcitrate, castor oil, acetylated monoglycerides, acetyl triethylcitrate, acetyl butylcitrate, diethyl phthalate, dibutyl phthalate, triacetin, fractionated coconut oil (medium-chain triglycerides).

The second layer containing the active ingredient may be comprised of the active ingredient (drug) with or without a polymer as a binder. The binder, when used, is usually hydrophilic but may be water-soluble or water-insoluble. Exemplary polymers to be used in the second layer containing the active drug are hydrophilic polymers such as polyvinylpyrrolidone, polyalkylene glycol such as polyethylene glycol, gelatine, polyvinyl alcohol, starch and derivatives thereof, cellulose derivatives, such as hydroxypropylmethyl cellulose (HPMC), hydroxypropyl cellulose, carboxymethyl cellulose, methyl cellulose, ethyl cellulose, hydroxyethyl cellulose, carboxyethyl cellulose, carboxymethyl hydroxyethyl cellulose, acrylic acid polymers, polymethacrylates, or any other pharmaceutically acceptable polymer. The ratio of drug to hydrophilic polymer in the second layer is usually in the range of from 1:100 to 100:1 (w/w).

Suitable polymers for use in the third layer, or membrane, for controlling the drug release may be selected from water insoluble polymers or polymers with pH-dependent solubility, such as, for example, ethyl cellulose, hydroxypropylmethyl cellulose phthalate, cellulose acetate phthalate, cellulose acetate trimellitate, polymethacrylates, or mixtures thereof, optionally combined with plasticizers, such as those mentioned above.

Optionally, the controlled release layer comprises, in addition to the polymers above, another substance(s) with different solubility characteristics, to adjust the permeability, and thereby the release rate, of the controlled release layer. Exemplary polymers that may be used as a modifier together with, for example, ethyl cellulose include: HPMC, hydroxyethyl cellulose, hydroxypropyl cellulose, methylcellulose, carboxymethylcellulose, polyethylene glycol, polyvinylpyrrolidone (PVP), polyvinyl alcohol, polymers with pH-dependent solubility, such as cellulose acetate phthalate or ammonio methacrylate copolymer and methacrylic acid copolymer, or mixtures thereof. Additives such as sucrose, lactose and pharmaceutical grade surfactants may also be included in the controlled release layer, if desired.

Also provided herein are unit dosage forms of the compositions. In such forms, the composition of the present disclosure is subdivided into unit dosages containing appropriate quantities of the active component (e.g., and without limitation, a compound of Formula (I) or an ester thereof, or a salt of each thereof). The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa.

Other Actives

A formulation (or kit) in accordance with the disclosure may contain, in addition to ibudilast and riluzole, one or more additional active agents effective in treating progressive neurodegenerative diseases. Preferably, the active agent is one that possesses a mechanism of action different from that of ibudilast and riluzole. Such actives include the combinations for pain listed in US Application No. 20060160843, as well as the active ingredients recognized for treatment for the target diseases. Such active ingredients can be found listed in the FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

Animal Models

The ability of compositions of the present disclosure to treat neurodegenerative diseases or disorders can be evaluated by any of the standard progressive neuropathic disease models known in the art. Examples of such models are described in Animal Models of Neurological Disease: Neurodegenerative Diseases (Neuromethods) by Alan A. Boulton, Glen B. Baker, and Roger F. Butterworth (1992); Handbook of Laboratory Animal Science, Second Edition: Volumes I-III (Handbook of Laboratory Animal Science) by Jann Hau (Editor), Jr., Gerald L. Van Hoosier (Editor). (2004); Animal Models of Movement Disorders by Mark LeDoux (Editor), (2005); and Animal Models of Cognitive Impairment (Frontiers in Neuroscience) (2006) by Edward D. Levin (Editor), Jerry J. Buccafusco (Editor).

Kits

Also provided herein is a kit containing at least one combination composition of the disclosure, accompanied by instructions for use.

For example, in instances in which each of the drugs themselves are administered as individual or separate dosage forms, the kit comprises ibudilast and riluzole, along with instructions for use. The ibudilast and riluzole may be packaged in any manner suitable for administration, so long as the packaging, when considered along with the instructions for administration, clearly indicates the manner in which each of the drug components is to be administered.

For example, in an illustrative kit comprising ibudilast and riluzole, the kit may be organized by any appropriate time period, such as by day. As an example, for Day 1, a representative kit may comprise unit dosages of each of ibudilast and riluzole. If each of the drugs is to be administered twice daily, then the kit may contain, corresponding to Day 1, two rows of unit dosage forms of each of ibudilast and riluzole, along with instructions for the timing of administration. Alternatively, if ibudilast and riluzole differ in the timing or quantity of administration, then such would be reflected in the packaging and instructions. Various embodiments according to the above may be readily envisioned, and would of course depend upon the particular combination of drugs, in addition to ibudilast and riluzole, employed for treatment, their corresponding dosage forms, recommended dosages, intended patient population, and the like. The packaging may be in any form commonly employed for the packaging of pharmaceuticals, and may utilize any of a number of features such as different colors, wrapping, tamper-resistant packaging, blister packs, dessicants, and the like.

It is to be understood that while the disclosure has been described in conjunction with preferred specific embodiments, the foregoing description as well as the examples that follow are intended to illustrate and not limit the scope of the disclosure. Other aspects, advantages and modifications within the scope of the disclosure will be apparent to those skilled in the art to which the disclosure pertains.

All references mentioned in this application, including any patents, published patent applications, books, handbooks, journal publications, or the FDA Orange Book are hereby incorporated by reference herein, in their entirety.

EXAMPLES

Example 1

Drosophila Life Span Assay as an ALS Treatment Model

Drosophila males will be collected. Flies will be transferred to fresh food (with active compounds) every 2-3 days. Daily, the number of living flies are analyzed. The experiment is performed under temperature controlled conditions (25° C.) and uses negative control (only solvent), and positive controls (wt stock, any antioxidant compound reported as able to increase life span in this fly model). In order to compare the activity of the testing compounds with riluzole by itself (an FDA-approved drug for ALS), this drug will be added to the assay.

The experiment includes the analysis of different compound concentrations of ibudilast and riluzole, each at different concentrations and will evaluate 240 flies for each concentration. Recovering on life span curve can indicate positive compound activity. See, FIG. 1.

Timing: 5 months (1-2 months to expand the fly stock and 3 months for assay execution and results interpretation).

Example 2

Drosophila Paraquat Sensitivity Assay as an ALS Treatment Model

Drosophila males will be collected and keep on fly food for 24 h. Then flies will be transferred to vials containing 3-mm paper filter disks saturated with 250 µl of 1% sucrose containing 2 mM paraquat or 1% sucrose, 2 mM paraquat and the tested compounds. The vials will be stored at 25° C. in the dark, and flies are enumerated after 24 h.

Three replicas for each concentration will be performed in the same day and three replicas of the assay will be performed in different days. A negative control (only solvent), and positive controls (wt stock, any antioxidant compound reported as able to increase life span in this fly model), and riluzole will be added to the assay.

Figure 2:
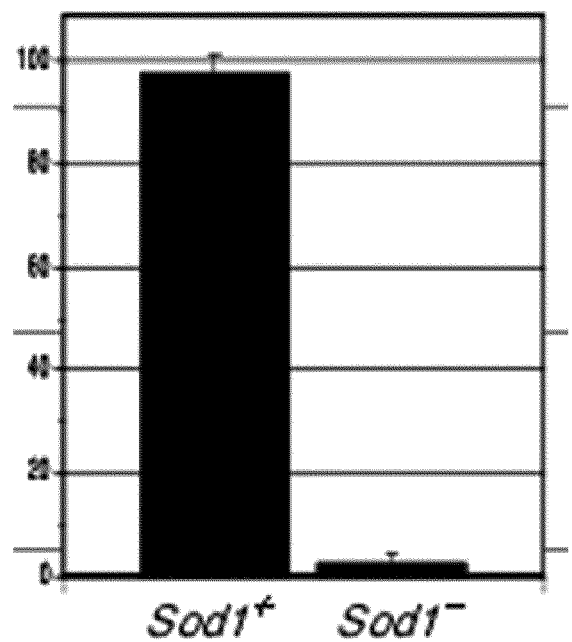
FIG. 2 graphically illustrates high (% viability) sensitivity of SOD1-null adults compared to a wild stock after exposure of adult flies to 2 mmol of paraquat. Resistance to paraquat treatment can indicate positive activity of the compound tested.

The experiment will test different compound of ibudilast-riluzole combinations and will evaluate 360 flies for each concentration. Resistance to paraquat treatment will be indicative of positive activity of the combinations tested. See, FIG. 2.

Timing: 10 weeks (1-2 months to expand the fly stock, two weeks for assay execution and results interpretation)

Example 3

Evaluation of Anti-ALS Activity On VAP-33A Drosophila Mutants

From other mutant stocks available and involving other ALS linked genes, loss of function of Vap-33-1 gene (excision of transcribed sequence and loss of protein function) displays valid fly phenotypes for evaluation of compounds activity. Indistinctly, Vap-33A$^{\Delta 448}$ or Vap-33A$^{\Delta 20}$ stocks display neurophysiology defects linked to a lethal phenotype during larvae development.

Viability assay

Vap-33A$^{\Delta}$ mutants are larval lethal with rare adult escapers (~1%)[7]. Embryos or larvae at stage 1 will be seeded on fly food with different compound concentrations of ibudilast-riluzole combinations. Three replicas for each combination will be performed in the same day. Three replicas of the assay will be performed in different days. Number of adult escapers will be quantified after 14 days of compound treatment. A negative control (only solvent), and positive controls (wt stock, any antioxidant compound reported as able to increase life span in this fly model), and riluzole will be added to the assay.

The experiment includes the analysis of four compound combinations and will evaluate 180 flies for each concentration (4 replicates×3 days with 15 flies each one).

Timing: 3 months (2 months to expand the fly stock, 1 month for assay execution and results interpretation

Example 4

Evaluation of Ibudilast-riluzole Combination in a Rat Model of Alzheimer's Disease A rat animal model for Alzheimer's disease is administered ibudilast and riluzole and an increase brain mass is achieved for the group of animals being administered ibudilast and riluzole, thereby indicating that this model can be effective for the treatment of Alzheimer' disease in humans.

Example 5

Evaluation of Ibudilast-riluzole Combination in a Rat Model of ALS

An animal model for ALS is administered ibudilast and riluzole and an increase brain mass is achieved for this group, thereby indicating that this model can be effective for the treatment ALS.

Example 6

Evaluation of Ibudilast-riluzole Combination in a Rat Model of Parkinson's Disease An animal model for Parkinson's disease is administered ibudilast and riluzole and an increase brain mass is achieved for this group, thereby indicating that this model can be effective for the treatment Parkinson's disease.

Example 7

Clinical Trial of the Ibudilast-riluzole Combination to Evaluate Its Effectiveness In Alzheimer's Disease A combination of ibudilast and riluzole is administered to patients exhibiting the symptoms of Alzheimer's disease, as diagnosed by their physician and confirmed by an independent board-certified neurologist. Prior to the clinical trial, the patients undergo appropriate psychoneurological tests such as the Mini Mental Status Exam (MMSE), the Alzheimer Disease Assessment Scale (ADAS), the Boston Naming Test (BNT), and the Token Test (TT). Neuropsychological tests are repeated at appropriate points during the clinical trial. The tests are performed by neuropsychologists who are not aware of the patients' treatment regimen.

In this double blind study, patients are randomly assigned to the test group or placebo group at the beginning of the study. The ibudilast or a pharmaceutically acceptable salt thereof and riluzole or a pharmaceutically acceptable salt thereof and placebo are administered orally at pre-designated intervals. The test patients are evaluated for a specified period of time to determine the effectiveness of treatment using the composition as compared to the control group individuals given a placebo. Scores are statistically compared between the test composition and the placebo for each of the three observational periods. Without treatment, the natural course of Alzheimer's disease results in significant deterioration of a patient's test scores during the course of the clinical trial. A patient treated with the combination of the disclosure is considered improved if the patient's scores remain the same or improve compared to placebo during the course of the clinical trial.

Example 8

Clinical Trial of the Ibudilast-riluzole Combination to Evaluate Its Effectiveness in ALS A combination of ibudilast and riluzole is administered to patients exhibiting the symptoms of ALS. In a double blind study, ibudilast and riluzole, or pharmaceutically acceptable salts thereof and placebo are administered orally at pre-designated intervals to a patient group and a placebo group, respectively. The test patients are evaluated for a specified period of time to determine the effectiveness of treatment using the combination as compared to the control group individuals given a placebo. The TUFTS Quantitative Neuromuscular Examination (TQNE) is a well standardized, reliable, validated test to measure strength and function in ALS. The test involves measurement of maximum voluntary isometric contraction (MVIC) of 8 muscle groups in the arms using a strain gauge tensiometer. This measurement is a standard for clinical trials in ALS. The ALS Functional Rating Scale (ALSFRS) is an rating scale used to determine patients' assessment of their ability and independence in 10 functional activities. Validity has been established by correlating ALSFRS scores with change in strength over time. The ALSFRS is generally a secondary outcome measure in clinical trials. A patient treated with the composition is considered improved if the patient's scores remain the same or improve compared to placebo during the course of the clinical trial.

Example 9

Clinical Trial of the Ibudilast-riluzole Combination to Evaluate Its Effectiveness in Parkinson's Disease A combination of ibudilast and riluzole is administered to patients exhibiting the symptoms of Parkinson's disease. In a double blind study, ibudilast and riluzole, or pharmaceutically acceptable salts thereof, and placebo are administered orally at pre-designated intervals to a patient group and a placebo group. The test patients are evaluated for a specified period of time to determine the effectiveness of treatment using the combination as compared to the control group individuals given a placebo. The prespecified primary efficacy outcome for Parkinson's disease is a change in the Activities of Daily Living and Motor components of the generally accepted Unified Parkinson's Disease Rating Scale (UPDRS II/III) between baseline and the last evaluation on treatment. Other assessment scales such as the UPDRS component scores (mental, motor, ADL), the modified Hoehn and Yahr Stage, Modified Schwab and England ADL score may be used to evaluate the efficacy of the present disclosure.

Example 10

Clinical Trial of the Ibudilast-riluzole Combination to Evaluate Its Effectiveness In Multiple Sclerosis A combination of ibudilast and riluzole is administered to patients exhibiting the symptoms of multiple sclerosis. In a double blind study, ibudilast and riluzole, or pharmaceutically acceptable salts thereof, and placebo are administered orally at pre-designated intervals to a patient group and a placebo group. A clinical trial will include multiple sclerosis patients diagnosed on McDonald criteria, with a baseline Expanded Disability Status Scale (EDDS) between 0 and 5 and either at least one relapse within the last 12 months of randomization and a previous MRI scanning showing lesions consistent with multiple sclerosis or Gd E lesions on MRI scan done within 6 months of randomization.

The primary endpoint for the clinical trial is time-to-confirmed disease progression or treatment failure as measured by EDSS or Multiple Sclerosis Functional Composite Score. Secondary endpoints include relapse rate-related endpoints and MRI measurement-related endpoints. Other tertiary endpoints may be measured, including cognitive function-related endpoints and quality of life-related endpoints.

Embodiments

1. A method of alleviating negative effects of a neurodegenerative disease or disorder in a human patient suffering therefrom, comprising administering to the human patient:
   (a) a therapeutically effective amount of ibudilast or a pharmaceutically acceptable salt thereof, and
   (b) a therapeutically effective amount of riluzole or a pharmaceutically acceptable salt thereof.

2. The method of Embodiment 1, in which the ibudilast or pharmaceutically acceptable salt thereof and the riluzole or pharmaceutically acceptable salt thereof are administered in separate dosage forms.

3. The method of Embodiment 1, in which the ibudilast or pharmaceutically acceptable salt thereof and the riluzole or pharmaceutically acceptable salt thereof are administered in the same dosage form.

4. The method of any one of Embodiments 1-3, in which the ibudilast or a pharmaceutically acceptable salt thereof and the riluzole or a pharmaceutically acceptable salt thereof are administered orally.

5. The method of any one of Embodiments 1-4, in which the ibudilast or a pharmaceutically acceptable salt thereof and the riluzole or a pharmaceutically acceptable salt thereof are administered in a tablet or a capsule dosage form.

6. The method of any one of Embodiments 1-5, in which the ibudilast or a pharmaceutically acceptable salt thereof and the riluzole or a pharmaceutically acceptable salt thereof are administered in a liquid dosage form.

7. The method of any one of Embodiments 1-6, wherein the ibudilast or a pharmaceutically acceptable salt thereof is administered in an amount from about 100 mg/day to about 4,000 mg/day, divided into one, two, or three portions.

8. The method of any one of Embodiments 1-7, in which the riluzole or a pharmaceutically acceptable salt thereof is administered in an amount from about 1 mg/kg/day to about 1000 mg/kg/day of the patient, divided into one, two, or three portions.

9. The method of any one of Embodiments 1-8, wherein the neurodegenerative disease or disorder compromises the nervous system.

10. The method of any one of Embodiments 1-9, wherein the neurodegenerative disease or disorder is Alzheimer's disease, Senile dementia of the Alzheimer type, Pick's disease (lobar atrophy), syndromes combining progressive dementia with other prominent neurologic abnormalities, Huntington's disease, multiple system atrophy combining dementia with ataxia and/or manifestation of Parkinson's disease, progressive supranuclear palsy (Steele-Richardson-Olszewski), diffuse Lewy body disease, corticodentatinigral degeneration, Hallervorden-Spatz disease, progressive familial myoclonic epilepsy, symptoms of gradually developing abnormalities of posture and movement, paralysis agitans (Parkinson's disease), striatonigral degeneration, progressive supranuclear palsy, torsion dystonia (torsion spasm; dystonia musculorum deformans), spasmodic torticollis and other restricted dyskinesias, Familial tremor, Gilles de la Tourette syndrome, progressive ataxia, cerebellar degenerations, spinocerebellar degenerations, cerebellar cortical degeneration, olivopontocerebellar atrophy (OPCA), spinocerebellar degenerations (Friedreich's ataxia and related disorders), central autonomic nervous system failure (Shy-Drager syndrome), syndromes of muscular weakness and wasting without sensory changes (motor neuron disease), amyotrophic lateral sclerosis (ALS), spinal muscular atrophy, infantile spinal muscular atrophy (Werdnig-Hoffmann), juvenile spinal muscular atrophy (Wohlfart-Kugelberg-Welander), other forms of familial spinal muscular atrophy, primary lateral sclerosis, hereditary spastic paraplegia, syndromes combining muscular weakness and wasting with sensory changes (progressive neural muscular atrophy; chronic familial polyneuropathies), peroneal muscular atrophy (Charcot-Marie-Tooth), hypertrophic interstitial polyneuropathy (Deferine-Sottas), or miscellaneous forms of chronic progressive neuropathy, syndromes of progressive visual loss, pigmentary degeneration of the retina (retinitis pigmentosa), hereditary optic atrophy (Leber's disease), Parkinson's disease and other extrapyramidal disorders, progressive supranuclear palsy (Steele-Richardson-Olszewski syndrome), torsion dystonia (torsion spasm, dystonia musculorum deformans), focal dystonias, motor neuron disease, progressive ataxias, primary lateral sclerosis, multifocal motor neuropathy with conduction block, motor neuropathy with paraproeinemia, motor-predominant peripheral neuropathies, olivopontocerebellar atrophy, Azorean (Machado-Joseph) disease, familial progressive neurodegenerative diseases, familial amyotrophic lateral sclerosis, spinal muscular atrophies, familial spastic paraparesis, hereditary biochemical disorders, arthrogryposis muliplex congenital, or progressive juvenile bulbar palsy (Fazio-Londe), infantile (Werdnig-Hoffman disease), childhood onset, or adolescent (Wohlfart-Kugelberg-Welander disease), familial HTLV-1 myelopathy, isolated FSP, or complicated FSP, superoxide dismutase deficiency, hexosaminidase A and B deficiency, androgen receptor mutation (Kennedy's syndrome), viral and prion diseases, myelopathy, progressive multifocal leukoencephalopathy, Creutzfeldt-Jakob disease, Gerstmann-Straussler-Scheinker disease, kuru, fatal familial insomnia, Alper's disease, primary progressive or secondary progressive multiple sclerosis, but not relapsing, remitting multiple sclerosis, frontotemporal dementia, Wilson's disease, progressive neuropathic pain, ischemia caused by stroke, traumatic brain injury, or spinal cord injury.

11. The method of any one of Embodiments 1-10, wherein the neurodegenerative disease or disorder is Alzheimer's disease, Parkinson's disease, amyotrophic lateral sclerosis (ALS), or multiple sclerosis.

12. The method of any one of Embodiments 1-11, wherein the neurodegenerative disease or disorder is ALS.

13. The method of any one of Embodiments 1-12, wherein the ibudilast and the riluzole, or pharmaceutically acceptable salts thereof, are administered simultaneously.

14. The method of any one of Embodiments 1-12, wherein the ibudilast and the riluzole, or pharmaceutically acceptable salts thereof, are administered consecutively.

15. A method of slowing progression of disease in a patient diagnosed with a chronic neurodegenerative disease, comprising administering to the patient:
   (a) a therapeutically effective amount of ibudilast or a pharmaceutically acceptable salt thereof, and
   (b) a therapeutically effective amount of riluzole or a pharmaceutically acceptable salt thereof.

16. The method of Embodiment 15, in which the ibudilast or a pharmaceutically acceptable salt thereof and the riluzole or a pharmaceutically acceptable salt thereof are administered orally.

17. The method of any one of Embodiments 15-16, wherein the neurodegenerative disease compromises the nervous system.

18. The method of any one of Embodiments 15-17, wherein the neurodegenerative disease is Alzheimer's disease, Senile dementia of the Alzheimer type, Pick's disease (lobar atrophy), syndromes combining progressive dementia with other prominent neurologic abnormalities, Huntington's disease, multiple system atrophy combining dementia with ataxia and/or manifestation of Parkinson's disease, progressive supranuclear palsy (Steele-Richardson-Olszewski), diffuse Lewy body disease, corticodentatinigral degeneration, Hallervorden-Spatz disease, progressive familial myoclonic epilepsy, symptoms of gradually developing abnormalities of posture and movement, paralysis agitans (Parkinson's disease), striatonigral degeneration, progressive supranuclear palsy, torsion dystonia (torsion spasm; dystonia musculorum deformans), spasmodic torticollis and other restricted dyskinesias, Familial tremor, Gilles de la Tourette syndrome, progressive ataxia, cerebellar degenerations, spinocerebellar degenerations, cerebellar cortical degeneration, olivopontocerebellar atrophy (OPCA), spinocerebellar degenerations (Friedreich's ataxia and related disorders), central autonomic nervous system failure (Shy-Drager syndrome), syndromes of muscular weakness and wasting without sensory changes (motor neuron disease), amyotrophic lateral sclerosis (ALS), spinal muscular atrophy, infantile spinal muscular atrophy (Werdnig-Hoffmann), juvenile spinal muscular atrophy (Wohlfart-Kugelberg-Welander), other forms of familial spinal muscular atrophy, primary lateral sclerosis, hereditary spastic paraplegia, syndromes combining muscular weakness and wasting with sensory changes (progressive neural muscular atrophy; chronic familial polyneuropathies), peroneal muscular atrophy (Charcot-Marie-Tooth), hypertrophic interstitial polyneuropathy (Deferine-Sottas), or miscellaneous forms of chronic progressive neuropathy, syndromes of progressive visual loss, pigmentary degeneration of the retina (retinitis pigmentosa), hereditary optic atrophy (Leber's disease), Parkinson's disease and other extrapyramidal disorders, progressive supranuclear palsy (Steele-Richardson-Olszewski syndrome), torsion dystonia (torsion spasm, dystonia musculorum deformans), focal dystonias, motor neuron disease, progressive ataxias, primary lateral sclerosis, multifocal motor neuropathy with conduction block, motor neuropathy with paraproeinemia, motor-predominant peripheral neuropathies, olivopontocerebellar atrophy, Azorean (Machado-Joseph) disease, familial progressive neurodegenerative diseases, familial amyotrophic lateral sclerosis, spinal muscular atrophies, familial spastic paraparesis, hereditary biochemical disorders, arthrogryposis muliplex congenital, or progressive juvenile bulbar palsy (Fazio-Londe), infantile (Werdnig-Hoffman disease), childhood onset, or adolescent (Wohlfart-Kugelberg-Welander disease), familial HTLV-1 myelopathy, isolated FSP, or complicated FSP, superoxide dismutase deficiency, hexosaminidase A and B deficiency, androgen receptor mutation (Kennedy's syndrome), viral and prion diseases, myelopathy, progressive multifocal leukoencephalopathy, Creutzfeldt-Jakob disease, Gerstmann-Straussler-Scheinker disease, kuru, fatal familial insomnia, Alper's disease, primary progressive or secondary progressive multiple sclerosis, but not relapsing, remitting multiple sclerosis, frontotemporal dementia, Wilson's disease, progressive neuropathic pain, ischemia caused by stroke, traumatic brain injury, or spinal cord injury.

19. The method of any one of Embodiments 15-18, wherein the neurodegenerative disease or disorder is Alzheimer's disease, Parkinson's disease, amyotrophic lateral sclerosis (ALS), or multiple sclerosis.

20. The method of any one of Embodiments 15-19, wherein the neurodegenerative disease or disorder is ALS.

21. The method of any one of Embodiments 15-20, wherein the ibudilast and the riluzole are administered simultaneously.

22. The method of any one of Embodiments 15-21, wherein the ibudilast and the riluzole are administered consecutively.

23. A composition for oral administration, comprising:
   (a) ibudilast or a pharmaceutically acceptable salt thereof,
   (b) riluzole or a pharmaceutically acceptable salt thereof, and
   (c) optionally, a pharmaceutically acceptable excipient or carrier.

24. The composition of Embodiment 23, comprising ibudilast or a pharmaceutically acceptable salt thereof in an amount from about 100 mg to about 4,000 mg, divided into one, two, or three portions.

25. The composition of any one of Embodiments 23-24, comprising riluzole or a pharmaceutically acceptable salt thereof in an amount from about 50 mg to about 4,000 mg, divided into one, two, or three portions.

26. The composition of any one of Embodiments 23-25, comprising from about 100 mg to about 4,000 mg of ibudilast or a pharmaceutically acceptable salt thereof and from about 50 mg to about 4,000 mg of riluzole or a pharmaceutically acceptable salt thereof. 27. The composition of any one of Embodiments 23-26, wherein the ibudilast and the riluzole are in a single tablet or a single capsule dosage form.

28. The composition of any one of Embodiments 23-27, wherein the ibudilast and the riluzole are in a liquid dosage form.

29. A method of treating a patient diagnosed with a neurodegenerative disease or disorder, comprising administering to a patient in need thereof:
   (a) a therapeutically effective amount of ibudilast or a pharmaceutically acceptable salt thereof, and
   (b) a therapeutically effective amount of riluzole or a pharmaceutically acceptable salt thereof.

30. The method of Embodiment 29, in which the ibudilast or a pharmaceutically acceptable salt thereof and riluzole or a pharmaceutically acceptable salt thereof are administered orally.

31. The method of any one of Embodiments 29-30, in which the ibudilast or a pharmaceutically acceptable salt thereof and riluzole or a pharmaceutically acceptable salt thereof are administered in a tablet or a capsule.

32. The method of any one of Embodiments 29-30, in which the ibudilast or a pharmaceutically acceptable salt thereof and riluzole or a pharmaceutically acceptable salt thereof are administered in a liquid dosage form.

33. The method of any one of Embodiments 29-32, wherein the ibudilast or a pharmaceutically acceptable salt thereof is administered in an amount from about 100 mg to about 4,000 mg/day, divided into one, two, or three portions.

34. The method of any one of Embodiments 29-33, in which the riluzole or pharmaceutically acceptable salt thereof is administered in an amount from about 1 mg/kg/day to about 1000 mg/kg/day of the patient, divided into one, two, or three portions.

35. The method of any one of Embodiments 29-34, wherein the neurodegenerative disease or disorder compromises the nervous system.

36. The method of any one of Embodiments 29-35, wherein the neurodegenerative disease or disorder is Alzheimer's disease, Senile dementia of the Alzheimer type, Pick's disease (lobar atrophy), syndromes combining progressive dementia with other prominent neurologic abnormalities, Huntington's disease, multiple system atrophy combining dementia with ataxia and/or manifestation of Parkinson's disease, progressive supranuclear palsy (Steele-Richardson-Olszewski), diffuse Lewy body disease, corticodentatinigral degeneration, Hallervorden-Spatz disease, progressive familial myoclonic epilepsy, symptoms of gradually developing abnormalities of posture and movement, paralysis agitans (Parkinson's disease), striatonigral degeneration, progressive supranuclear palsy, torsion dystonia (torsion spasm; dystonia musculorum deformans), spasmodic torticollis and other restricted dyskinesias, Familial tremor, Gilles de la Tourette syndrome, progressive ataxia, cerebellar degenerations, spinocerebellar degenerations, cerebellar cortical degeneration, olivopontocerebellar atrophy (OPCA), spinocerebellar degenerations (Friedreich's ataxia and related disorders), central autonomic nervous system failure (Shy-Drager syndrome), syndromes of muscular weakness and wasting without sensory changes (motor neuron disease), amyotrophic lateral sclerosis (ALS), spinal muscular atrophy, infantile spinal muscular atrophy (Werdnig-Hoffmann), juvenile spinal muscular atrophy (Wohlfart-Kugelberg-Welander), other forms of familial spinal muscular atrophy, primary lateral sclerosis, hereditary spastic paraplegia, syndromes combining muscular weakness and wasting with sensory changes (progressive neural muscular atrophy; chronic familial polyneuropathies), peroneal muscular atrophy (Charcot-Marie-Tooth), hypertrophic interstitial polyneuropathy (Deferine-Sottas), or miscellaneous forms of chronic progressive neuropathy, syndromes of progressive visual loss, pigmentary degeneration of the retina (retinitis pigmentosa), hereditary optic atrophy (Leber's disease), Parkinson's disease and other extrapyramidal disorders, progressive supranuclear palsy (Steele-Richardson-Olszewski syndrome), torsion dystonia (torsion spasm, dystonia musculorum deformans), focal dystonias, motor neuron disease, progressive ataxias, primary lateral sclerosis, multifocal motor neuropathy with conduction block, motor neuropathy with paraproeinemia, motor-predominant peripheral neuropathies, olivopontocerebellar atrophy, Azorean (Machado-Joseph) disease, familial progressive neurodegenerative diseases, familial amyotrophic lateral sclerosis, spinal muscular atrophies, familial spastic paraparesis, hereditary biochemical disorders, arthrogryposis muliplex congenital, or progressive juvenile bulbar palsy (Fazio-Londe), infantile (Werdnig-Hoffman disease), childhood onset, or adolescent (Wohlfart-Kugelberg-Welander disease), familial HTLV-1 myelopathy, isolated FSP, or complicated FSP, superoxide dismutase deficiency, hexosaminidase A and B deficiency, androgen receptor mutation (Kennedy's syndrome), viral and prion diseases, myelopathy, progressive multifocal leukoencephalopathy, Creutzfeldt-Jakob disease, Gerstmann-Straussler-Scheinker disease, kuru, fatal familial insomnia, Alper's disease, primary progressive or secondary progressive multiple sclerosis, but not relapsing, remitting multiple sclerosis, frontotemporal dementia, Wilson's disease, progressive neuropathic pain, ischemia caused by stroke, traumatic brain injury, or spinal cord injury.

37. The method of any one of Embodiments 29-36, wherein the neurodegenerative disease or disorder is Alzheimer's disease, Parkinson's disease, amyotrophic lateral sclerosis (ALS), or multiple sclerosis.

38. The method of any one of Embodiments 29-37, wherein the neurodegenerative disease or disorder is ALS.

39. The method of any one of Embodiments 29-38, wherein the ibudilast and the riluzole are administered simultaneously.

40. The method of any one of Embodiments 29-38, wherein the ibudilast and the riluzole are administered consecutively in any order.

41. A method of reducing a volume of an infarct (an area of necrosis in a tissue or organ resulting from obstruction of the local circulation by a thrombus or embolus) in a patient suffering from an ischemia, comprising administering to a patient in need thereof:
   (a) a therapeutically effective amount of ibudilast or a pharmaceutically acceptable salt thereof, and
   (b) a therapeutically effective amount of riluzole or a pharmaceutically acceptable salt thereof,
in which a volume of an infarct in the treated patient is reduced compared to a volume of an infarct in a control patient.

42. The method of Embodiment 41, in which the ibudilast or a pharmaceutically acceptable salt thereof and the riluzole or a pharmaceutically acceptable salt thereof are administered orally.

43. The method of any one of Embodiments 41-42, in which the ibudilast or a pharmaceutically acceptable salt thereof and riluzole or a pharmaceutically acceptable salt thereof are administered in a tablet or a capsule dosage form.

44. The method of any one of Embodiments 41-42, in which the ibudilast or a pharmaceutically acceptable salt thereof and the riluzole or a pharmaceutically acceptable salt thereof are administered in a liquid dosage form.

45. The method of any one of Embodiments 41-44, wherein the ibudilast or a pharmaceutically acceptable salt thereof is administered in an amount from about 100 mg to about 4,000 mg/day, divided into one, two, or three portions.

46. The method of any one of Embodiments 41-45, in which the riluzole or a pharmaceutically acceptable salt thereof is administered in an amount from about 1 mg/kg/day to about 1000 mg/kg/day of the patient, divided into one, two, or three portions.

47. The method of any one of Embodiments 41-46, wherein the ibudilast and the riluzole are administered simultaneously in a single dosage form.

48. The method of any one of Embodiments 41-47, wherein the ibudilast and the riluzole are administered in separate dosage forms.

49. A therapeutically effective amount of ibudilast or a pharmaceutically acceptable salt thereof and a therapeutically effective amount of riluzole or a pharmaceutically acceptable salt thereof for use in a method of alleviating negative effects of a neurodegenerative disease.

50. A therapeutically effective amount of ibudilast or a pharmaceutically acceptable salt thereof and a therapeutically effective amount of riluzole or a pharmaceutically acceptable salt thereof for use in a method of slowing progression of disease in a patient diagnosed with a chronic neurodegenerative disease.

51. A therapeutically effective amount of ibudilast or a pharmaceutically acceptable salt thereof and a therapeutically effective amount of riluzole or a pharmaceutically acceptable salt thereof for use in a method of treating a patient diagnosed with a neurodegenerative disease or disorder.

52. The therapeutically effective amount of ibudilast or a pharmaceutically acceptable salt thereof and the therapeutically effective amount of riluzole or a pharmaceutically acceptable salt thereof of any one of Embodiments 49-51, wherein the neurodegenerative disease or disorder is Alzheimer's disease, Senile dementia of the Alzheimer type, Pick's disease (lobar atrophy), syndromes combining progressive dementia with other prominent neurologic abnormalities, Huntington's disease, multiple system atrophy combining dementia with ataxia and/or manifestation of Parkinson's disease, progressive supranuclear palsy (Steele-Richardson-Olszewski), diffuse Lewy body disease, corticodentatinigral degeneration, Hallervorden-Spatz disease, progressive familial myoclonic epilepsy, symptoms of gradually developing abnormalities of posture and movement, paralysis agitans (Parkinson's disease), striatonigral degeneration, progressive supranuclear palsy, torsion dystonia (torsion spasm; dystonia musculorum deformans), spasmodic torticollis and other restricted dyskinesias, Familial tremor, Gilles de la Tourette syndrome, progressive ataxia, cerebellar degenerations, spinocerebellar degenerations, cerebellar cortical degeneration, olivopontocerebellar atrophy (OPCA), spinocerebellar degenerations (Friedreich's ataxia and related disorders), central autonomic nervous system failure (Shy-Drager syndrome), syndromes of muscular weakness and wasting without sensory changes (motor neuron disease), amyotrophic lateral sclerosis (ALS), spinal muscular atrophy, infantile spinal muscular atrophy (Werdnig-Hoffmann), juvenile spinal muscular atrophy (Wohlfart-Kugelberg-Welander), other forms of familial spinal muscular atrophy, primary lateral sclerosis, hereditary spastic paraplegia, syndromes combining muscular weakness and wasting with sensory changes (progressive neural muscular atrophy; chronic familial polyneuropathies), peroneal muscular atrophy (Charcot-Marie-Tooth), hypertrophic interstitial polyneuropathy (Deferine-Sottas), or miscellaneous forms of chronic progressive neuropathy, syndromes of progressive visual loss, pigmentary degeneration of the retina (retinitis pigmentosa), hereditary optic atrophy (Leber's disease), Parkinson's disease and other extrapyramidal disorders, progressive supranuclear palsy (Steele-Richardson-Olszewski syndrome), torsion dystonia (torsion spasm, dystonia musculorum deformans), focal dystonias, motor neuron disease, progressive ataxias, primary lateral sclerosis, multifocal motor neuropathy with conduction block, motor neuropathy with paraproeinemia, motor-predominant peripheral neuropathies, olivopontocerebellar atrophy, Azorean (Machado-Joseph) disease, familial progressive neurodegenerative diseases, familial amyotrophic lateral sclerosis, spinal muscular atrophies, familial spastic paraparesis, hereditary biochemical disorders, arthrogryposis muliplex congenital, or progressive juvenile bulbar palsy (Fazio-Londe), infantile (Werdnig-Hoffman disease), childhood onset, or adolescent (Wohlfart-Kugelberg-Welander disease), familial HTLV-1 myelopathy, isolated FSP, or complicated FSP, superoxide dismutase deficiency, hexosaminidase A and B deficiency, androgen receptor mutation (Kennedy's syndrome), viral and prion diseases, myelopathy, progressive multifocal leukoencephalopathy, Creutzfeldt-Jakob disease, Gerstmann-Straussler-Scheinker disease, kuru, fatal familial insomnia, Alper's disease, primary progressive or secondary progressive multiple sclerosis, but not relapsing, remitting multiple sclerosis, frontotemporal dementia, Wilson's disease, progressive neuropathic pain, ischemia caused by stroke, traumatic brain injury, or spinal cord injury.

53. The therapeutically effective amount of ibudilast or a pharmaceutically acceptable salt thereof and the therapeutically effective amount of riluzole or a pharmaceutically acceptable salt thereof of any one of Embodiments 49-52, wherein the neurodegenerative disease or disorder is Alzheimer's disease, Parkinson's disease, amyotrophic lateral sclerosis (ALS), or multiple sclerosis.

54. The therapeutically effective amount of ibudilast or a pharmaceutically acceptable salt thereof and the therapeutically effective amount of riluzole or a pharmaceutically acceptable salt thereof of any one of Embodiments 49-53, wherein the neurodegenerative disease or disorder is ALS.

55. A therapeutically effective amount of ibudilast or a pharmaceutically acceptable salt thereof and a therapeutically effective amount of riluzole or a pharmaceutically acceptable salt thereof for use in a method of reducing a volume of an infarct (an area of necrosis in a tissue or organ resulting from obstruction of the local circulation by a thrombus or embolus) in a patient suffering from an ischemia.

56. Use of a therapeutically effective amount of ibudilast or a pharmaceutically acceptable salt thereof and a therapeutically effective amount of riluzole or a pharmaceutically acceptable salt thereof in the manufacture of a medicament for alleviating negative effects of a neurodegenerative disease.

57. Use of a therapeutically effective amount of ibudilast or a pharmaceutically acceptable salt thereof and a therapeutically effective amount of riluzole or a pharmaceutically acceptable salt thereof in the manufacture of a medicament for slowing progression of disease in a patient diagnosed with a chronic neurodegenerative disease.

58. Use of a therapeutically effective amount of ibudilast or a pharmaceutically acceptable salt thereof and a therapeutically effective amount of riluzole or a pharmaceutically acceptable salt thereof in the manufacture of a medicament for treating a patient diagnosed with a neurodegenerative disease or disorder.

59. The use of any one of Embodiments 56-58, wherein the neurodegenerative disease or disorder is Alzheimer's disease, Senile dementia of the Alzheimer type, Pick's disease (lobar atrophy), syndromes combining progressive dementia with other prominent neurologic abnormalities, Huntington's disease, multiple system atrophy combining dementia with ataxia and/or manifestation of Parkinson's disease, progressive supranuclear palsy (Steele-Richardson-Olszewski), diffuse Lewy body disease, corticodentatinigral degeneration, Hallervorden-Spatz disease, progressive familial myoclonic epilepsy, symptoms of gradually developing abnormalities of posture and movement, paralysis agitans (Parkinson's disease), striatonigral degeneration, progressive supranuclear palsy, torsion dystonia (torsion spasm; dystonia musculorum deformans), spasmodic torticollis and other restricted dyskinesias, Familial tremor, Gilles de la Tourette syndrome, progressive ataxia, cerebellar degenerations, spinocerebellar degenerations, cerebellar cortical degeneration, olivopontocerebellar atrophy (OPCA), spinocerebellar degenerations (Friedreich's ataxia and related disorders), central autonomic nervous system failure (Shy-Drager syndrome), syndromes of muscular weakness and wasting without sensory changes (motor neuron disease), amyotrophic lateral sclerosis (ALS), spinal muscular atrophy, infantile spinal muscular atrophy (Werdnig-Hoffmann), juvenile spinal muscular atrophy (Wohlfart-Kugelberg-Welander), other forms of familial spinal muscular atrophy, primary lateral sclerosis, hereditary spastic paraplegia, syndromes combining muscular weakness and wasting with sensory changes (progressive neural muscular atrophy; chronic familial polyneuropathies), peroneal muscular atrophy (Charcot-Marie-Tooth), hypertrophic interstitial polyneuropathy (Deferine-Sottas), or miscellaneous forms of chronic progressive neuropathy, syndromes of progressive visual loss, pigmentary degeneration of the retina (retinitis pigmentosa), hereditary optic atrophy (Leber's disease), Parkinson's disease and other extrapyramidal disorders, progressive supranuclear palsy (Steele-Richardson-Olszewski syndrome), torsion dystonia (torsion spasm, dystonia musculorum deformans), focal dystonias, motor neuron disease, progressive ataxias, primary lateral sclerosis, multifocal motor neuropathy with conduction block, motor neuropathy with paraproeinemia, motor-predominant peripheral neuropathies, olivopontocerebellar atrophy, Azorean (Machado-Joseph) disease, familial progressive neurodegenerative diseases, familial amyotrophic lateral sclerosis, spinal muscular atrophies, familial spastic paraparesis, hereditary biochemical disorders, arthrogryposis muliplex congenital, or progressive juvenile bulbar palsy (Fazio-Londe), infantile (Werdnig-Hoffman disease), childhood onset, or adolescent (Wohlfart-Kugelberg-Welander disease), familial HTLV-1 myelopathy, isolated FSP, or complicated FSP, superoxide dismutase deficiency, hexosaminidase A and B deficiency, androgen receptor mutation (Kennedy's syndrome), viral and prion diseases, myelopathy, progressive multifocal leukoencephalopathy, Creutzfeldt-Jakob disease, Gerstmann-Straussler-Scheinker disease, kuru, fatal familial insomnia, Alper's disease, primary progressive or secondary progressive multiple sclerosis, but not relapsing, remitting multiple sclerosis, fronto-temporal dementia, Wilson's disease, progressive neuropathic pain, ischemia caused by stroke, traumatic brain injury, or spinal cord injury.

60. The use of any one of Embodiments 56-59, wherein the neurodegenerative disease or disorder is Alzheimer's disease, Parkinson's disease, amyotrophic lateral sclerosis (ALS), or multiple sclerosis.

61. The use of any one of Embodiments 56-60, wherein the neurodegenerative disease or disorder is ALS.

62. Use of a therapeutically effective amount of ibudilast or a pharmaceutically acceptable salt thereof and a therapeutically effective amount of riluzole or a pharmaceutically acceptable salt thereof in the manufacture of a medicament for reducing a volume of an infarct (an area of necrosis in a tissue or organ resulting from obstruction of the local circulation by a thrombus or embolus) in a patient suffering from an ischemia.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can of course vary. It is also to be understood that the terminology used herein is for the purpose of describing particular embodiments only, and is not intended to be limiting.

As will be understood by one skilled in the art, for any and all purposes, particularly in terms of providing a written description, all ranges disclosed herein also encompass any and all possible subranges and combinations of subranges thereof. For example, ranges describing isomeric ratios disclosed herein encompass any and all possible subranges of ratios thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A method of (i) alleviating negative effects of a neurodegenerative disease or disorder in a human patient suffering therefrom, or (ii) treating a patient diagnosed with a neurodegenerative disease or disorder, or (iii) slowing progression of disease in a patient diagnosed with a chronic neurodegenerative disease, comprising administering to the human patient or patient:
    (a) a therapeutically effective amount of ibudilast or a pharmaceutically acceptable salt thereof, and (b) a therapeutically effective amount of riluzole or a pharmaceutically acceptable salt thereof.

2. The method of claim 1, in which the ibudilast or pharmaceutically acceptable salt thereof and the riluzole or pharmaceutically acceptable salt thereof are administered in separate dosage forms or in the same dosage form.

3. The method of claim 1, in which the ibudilast or a pharmaceutically acceptable salt thereof and riluzole or a pharmaceutically acceptable salt thereof are administered orally.

4. The method of claim 3, in which the ibudilast or a pharmaceutically acceptable salt thereof and riluzole or a pharmaceutically acceptable salt thereof are administered in a tablet, a capsule, or a liquid dosage form.

5. The method of claim 1, wherein
(a) the ibudilast or a pharmaceutically acceptable salt thereof is administered in an amount from about 100 mg/day to about 4,000 mg/day, divided into one, two, or three portions; or
(b) the riluzole or a pharmaceutically acceptable salt thereof is administered in an amount from about 1 mg/kg/day to about 1000 mg/kg/day of the patient, divided into one, two, or three portions.

6. The method of claim 1, wherein the neurodegenerative disease or disorder or chronic neurodegenerative disease is Alzheimer's disease, Senile dementia of the Alzheimer type, Pick's disease (lobar atrophy), syndromes combining progressive dementia with other prominent neurologic abnormalities, Huntington's disease, multiple system atrophy combining dementia with ataxia and/or manifestation of Parkinson's disease, progressive supranuclear palsy (Steele-Richardson-Olszewski), diffuse Lewy body disease, corticodentatinigral degeneration, Hallervorden-Spatz disease, progressive familial myoclonic epilepsy, symptoms of gradually developing abnormalities of posture and movement, paralysis agitans (Parkinson's disease), striatonigral degeneration, progressive supranuclear palsy, torsion dystonia (torsion spasm; dystonia musculorum deformans), spasmodic torticollis and other restricted dyskinesias, Familial tremor, Gilles de la Tourette syndrome, progressive ataxia, cerebellar degenerations, spinocerebellar degenerations, cerebellar cortical degeneration, olivopontocerebellar atrophy (OPCA), spinocerebellar degenerations (Friedreich's ataxia and related disorders), central autonomic nervous system failure (Shy-Drager syndrome), syndromes of muscular weakness and wasting without sensory changes (motor neuron disease), amyotrophic lateral sclerosis (ALS), spinal muscular atrophy, infantile spinal muscular atrophy (Werdnig-Hoffmann), juvenile spinal muscular atrophy (Wohlfart-Kugelberg-Welander), other forms of familial spinal muscular atrophy, primary lateral sclerosis, hereditary spastic paraplegia, syndromes combining muscular weakness and wasting with sensory changes (progressive neural muscular atrophy; chronic familial polyneuropathies), peroneal muscular atrophy (Charcot-Marie-Tooth), hypertrophic interstitial polyneuropathy (Deferine-Sottas), or miscellaneous forms of chronic progressive neuropathy, syndromes of progressive visual loss, pigmentary degeneration of the retina (retinitis pigmentosa), hereditary optic atrophy (Leber's disease), Parkinson's disease and other extrapyramidal disorders, progressive supranuclear palsy (Steele-Richardson-Olszewski syndrome), torsion dystonia (torsion spasm, dystonia musculorum deformans), focal dystonias, motor neuron disease, progressive ataxias, primary lateral sclerosis, multifocal motor neuropathy with conduction block, motor neuropathy with paraproeinemia, motor-predominant peripheral neuropathies, olivopontocerebellar atrophy, Azorean (Machado-Joseph) disease, familial progressive neurodegenerative diseases, familial amyotrophic lateral sclerosis, spinal muscular atrophies, familial spastic paraparesis, hereditary biochemical disorders, arthrogryposis muliplex congenital, or progressive juvenile bulbar palsy (Fazio-Londe), infantile (Werdnig-Hoffman disease), childhood onset, or adolescent (Wohlfart-Kugelberg-Welander disease), familial HTLV-1 myelopathy, isolated FSP, or complicated FSP, superoxide dismutase deficiency, hexosaminidase A and B deficiency, androgen receptor mutation (Kennedy's syndrome), viral and prion diseases, myelopathy, progressive multifocal leukoencephalopathy, Creutzfeldt-Jakob disease, Gerstmann-Straussler-Scheinker disease, kuru, fatal familial insomnia, Alper's disease, primary progressive or secondary progressive multiple sclerosis, but not relapsing, remitting multiple sclerosis, frontotemporal dementia, Wilson's disease, progressive neuropathic pain, ischemia caused by stroke, traumatic brain injury, or spinal cord injury.

7. The method of claim 1, wherein the neurodegenerative disease or disorder or chronic neurodegenerative disease is Alzheimer's disease, Parkinson's disease, amyotrophic lateral sclerosis (ALS), or multiple sclerosis.

8. The method of claim 1, wherein the neurodegenerative disease or disorder or chronic neurodegenerative disease is ALS.

9. The method of claim 1, wherein the ibudilast and the riluzole, or pharmaceutically acceptable salts thereof, are administered simultaneously.

10. The method of claim 1, wherein the ibudilast and the riluzole, or pharmaceutically acceptable salts thereof, are administered consecutively.

* * * * *